United States Patent
Wimmer

(10) Patent No.: US 6,981,405 B2
(45) Date of Patent: Jan. 3, 2006

(54) MOISTURE-DETECTION DEVICE

(75) Inventor: Willi Wimmer, Hauzenberg (DE)

(73) Assignee: Vogt Electronic AG, Obernzell (DE)

( * ) Notice: Subject to any disclaimer, the term of this patent is extended or adjusted under 35 U.S.C. 154(b) by 98 days.

(21) Appl. No.: 10/163,503

(22) Filed: Jun. 7, 2002

(65) Prior Publication Data

US 2002/0189329 A1 Dec. 19, 2002

(30) Foreign Application Priority Data

Jun. 8, 2001 (DE) .................. 101 27 990

(51) Int. Cl.
*G01N 5/02* (2006.01)
*G01N 25/56* (2006.01)
(52) U.S. Cl. .................. 73/74; 73/73; 73/335.04
(58) Field of Classification Search .................. 73/74, 73/73, 335.4
See application file for complete search history.

(56) References Cited

U.S. PATENT DOCUMENTS

| | | | |
|---|---|---|---|
| 3,906,340 A | | 9/1975 | Wingfield et al. |
| 4,703,237 A | * | 10/1987 | Hochstein .................. 318/483 |
| 5,040,411 A | * | 8/1991 | Medzius .................. 73/73 |
| 5,672,976 A | * | 9/1997 | Egger et al. .................. 324/687 |
| 5,682,788 A | | 11/1997 | Netzer |

FOREIGN PATENT DOCUMENTS

| | | |
|---|---|---|
| DE | 3220123 A1 | 12/1983 |
| DE | 3437950 A1 | 4/1985 |
| DE | 44 26 736 A1 | 2/1996 |
| DE | 197 10 591 A1 | 9/1998 |
| DE | 19710591 A1 * | 9/1998 |

* cited by examiner

*Primary Examiner*—Hezron Williams
*Assistant Examiner*—André K. Jackson
(74) *Attorney, Agent, or Firm*—Birch, Stewart, Kolasch & Birch, LLP

(57) ABSTRACT

A device for determining moisture has an LC-oscillating circuit as a transducer and an oscillator for exciting the oscillating circuit. Further, the device for determining moisture has a tuning device for frequency-wise tuning the oscillator and a measuring and evaluation circuit to determine an attenuation condition of the oscillator and to provide a signal that is proportional to a degree of moisture at the transducer. The transducer and the oscillator are coupled in a contact-free manner.

19 Claims, 2 Drawing Sheets

MOISTURE-DETECTION DEVICE

BACKGROUND OF THE INVENTION

This application claims a priority from German application DE 101 27 990.6-52, filed on Jun. 8, 2001, and the contents of that application are incorporated herein by reference.

This invention concerns apparatus for detecting moisture of a type including an LC-oscillating circuit as a transducer, an oscillator for exciting the oscillating circuit, a tuning device for frequency-wise tuning of the oscillator, and a measuring and evaluation circuit to determine the attenuation, or dampened, condition of the oscillator and to provide a signal that is proportional to a relative, or degree of, moisture of the transducer.

Such a device for recognizing, or determining, moisture is disclosed in German Patent document DE 44 26 736 A1.

With the help of such a device, or such a sensor system, a windshield wiper of a motor vehicle can be controlled depending on an amount of rain, for example.

Known devices for determining moisture of the type described in German Patent document DE 44 26 736 A1, as well as known corresponding optical, resistive and capacitive sensor systems for determining moisture in other technical prior art, all have the disadvantage that they must be attached to a windshield of a motor vehicle in an expensive manner. The cost of electronic components for transducers is relatively great, which represents a particular disadvantage for fabrication of, as well as the breaking of, motor-vehicle windshields. Optical sensor systems have the additional disadvantage that they are very sensitive to dirt contamination, and therefore, an output signal of a measuring and evaluation circuit often can no longer be trusted as being a measurement of the degree of moisture at the transducer.

It is an object of this invention to provide a device for determining moisture that allows the greatest degree of freedom for mounting the transducer and with the transducer having the fewest possible electronic components, while it is also possible to assemble the measuring and evaluation circuit substantially independently of the transducer. In addition, it is an object of this invention to provide uses for such a device for determining moisture.

SUMMARY OF THE INVENTION

According to principles of this invention, in a device for determining moisture of the type set forth in the opening paragraph above, either the transducer and the oscillator have a contact-free energy coupling between them or the transducer consists of a single conductive lead, with such a device being used for determining moisture.

Further beneficial and preferred enhancements of the embodiments described above of devices for determining moisture of the invention are described herein.

BRIEF DESCRIPTION OF THE DRAWINGS

Further benefits, characteristics and details of the invention are explained in more detail below using embodiments shown in the drawings. The described and drawn features can be used individually or in preferred combinations in other embodiments of the invention. The foregoing and other objects, features and advantages of the invention will be apparent from the following more particular description of the preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 4a is a segmented cross-sectioned view of a windshield of FIG. 4.

DETAILED DESCRIPTION OF THE PREFERRED EMBODIMENT

Figure 1:
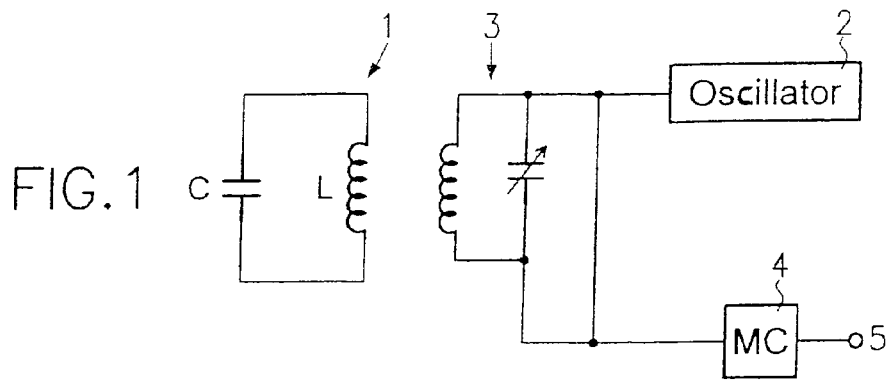
FIG. 1 is a conceptual schematic circuit/block diagram of an embodiment of a device for moisture detection of this invention.

The conceptual schematic diagram of FIG. 1 concerns an embodiment of a device for determining moisture of this invention.

The circuit includes an LC-oscillating circuit 1 as a transducer, as well as an oscillator 2 for exciting the oscillating circuit 1. Further, there is a tuner 3 for sweep-tuning the frequency of the oscillator 2 and there is a measuring and evaluation circuit 4. The measuring and evaluation circuit 4 records a dampened, or attenuation, condition of the oscillator 2 and provides a signal that is proportional to a degree of moisture, or a moisture ratio, or relative moisture, at the transducer 1. This signal is provided at the output 5.

In the embodiment of FIG. 1 the transducer 1 and the oscillator 2 have a contact-less energy coupling. In other embodiments of devices of this invention for determining moisture a coupling between the transducer 1 and the oscillator 2 can be a galvanic conductive path, in which case it is important that the transducer 1 is formed of a single conductive lead, as is further described below using FIGS. 3a–d.

Figure 2:
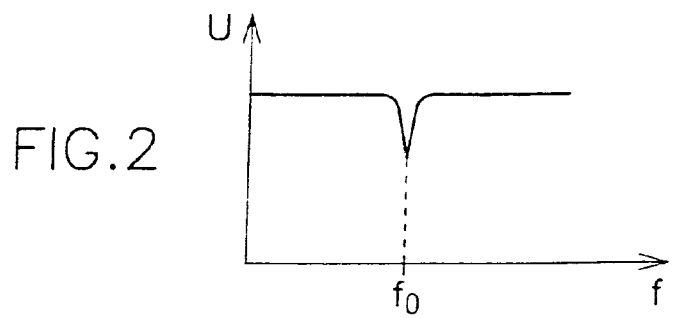
FIG. 2 is a conceptual frequency plot of an output voltage of the circuit of FIG. 1.

The tuning device, or circuit, 3 can be operated manually, however, it is preferably driven automatically. The tuning circuit 3 serves to tune the oscillator 2 frequency-wise, or sweep-wise. When the actual oscillator frequency corresponds to a resonance frequency $f_0$ of the transducer 1, a dampening, or attenuation, of the oscillator 2 is decidedly greater than when these two frequencies do not correspond. This large dampening at resonance leads to a clear reduction of a voltage U appearing at the output 5 of the circuit, as can be seen in FIG. 2.

Both components of the LC-oscillating circuit 1 are sensitive to moisture. If conductive material is located in a flux field of the oscillating circuit 1, eddy currents are created therein. These eddy currents cause, especially at higher frequencies, a feedback, or back voltage, in the induction L, whereby because of the back induction an impedance of the oscillating circuit 1 is changed. Thus, the induction is somewhat reduced because of the non-magnetic characteristics of the moisture, which in turn leads to a frequency increase that results in, as shown in equation (1):

$$f_0 = \frac{1}{2*\sqrt{L*C}} \tag{1}$$

The capacitance is affected in a similar manner. If a material with a high relative permittivity, or relative dielectric constant, (for example water $\epsilon_r=80$) comes close to the oscillating circuit 1, the capacitance C is increased. This results in a frequency reduction as can be seen from the applicable equation (2):

$$C = \varepsilon_0 \cdot \varepsilon_r \cdot \frac{A}{d}, \quad (2)$$

where $\epsilon_0$ and $\epsilon_r$ are respectively the absolute and relative dialectic constants, A is the condenser area and d is the spacing between the condenser plates.

The inductive reduction is, however, in comparison to the capacitance increase, negligible so that in total the resonance frequency of the LC-oscillating circuit 1 serving as the transducer is reduced due to moisture influence. This dependence is exploited in all of the devices for determining moisture of this invention.

In each of the embodiments, the resonance frequency $f_0$ of the oscillating circuit 1, and thereby the voltage U provided at the output 5 of the conceptual circuit of FIG. 1 has a frequency plot, or characteristic, that is dependent on surrounding quantities to be measured by the transducer, namely, the quantity of moisture.

In other embodiments of devices of this invention for determining moisture, the specific voltage curve U shown in FIG. 2 is not provided at the output 5 of the represented circuit, rather a still further processed signal from the measuring and evaluation circuit 4 that is proportional to a degree of moisture, or relative moisture, at the transducer 1 is provided. This signal can then further be used to control other devices, for example, windshield wipers, pumps, ventilators, or indicating devices.

Figure 3A:
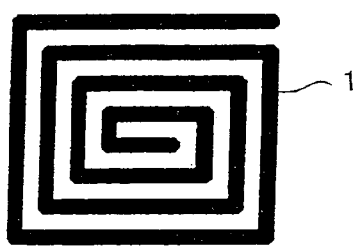
FIGS. 3a–d are schematic representations of different embodiments of transducers for use in a device for determining moisture of this invention.
Figure 3B:
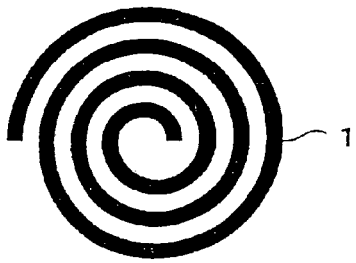
Figure 3C:
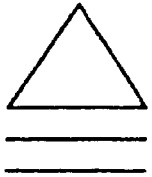
Figure 3D:
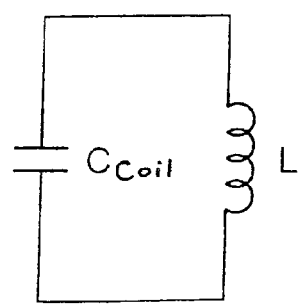

In FIGS. 3a–d, embodiments of transducers for particular devices of this invention for determining moisture are shown in which these transducers, respectively, distinguish themselves by each being formed of only one conductive lead. FIG. 3d shows a respective corresponding equivalent circuit diagram that is again exactly as the passive LC-oscillating circuit as already shown in FIG. 1. The special feature is that the self-capacitance of the conductive-lead arrangement is used to realize the capacitance C of the LC-oscillating circuit. In order to achieve the greatest possible change of frequency for moisture to be detected, care must be taken that the coil, or winding, capacitance is changed as much as possible by this amount, that is, by the moisture. This can be achieved in a particularly beneficial manner using planar coils, as shown in FIGS. 3a–b. In other embodiments the conductive lead, however, can be constructed in a conventional coil technique manner. The forms to be used are not limited to the geometrical shapes shown in FIGS. 3a and 3b. Rather, a large number of other forms are imaginable. It is known to those of ordinary skill in the art that each conductive lead arrangement continuously has a parasitic capacitance that is exploited in corresponding embodiments of devices for determining moisture according to this invention. Star-shaped arrangements are also possible, as well as arrangements which fit the form of an outer perimeter of a motor vehicle windshield. In this manner, for example, upon deployment of an appropriate embodiment of a device of this invention for determining moisture as a rain sensor for controlling a windshield wiper of a motor vehicle, the transducer can be adapted in a beneficial manner to have the geometry of the windshield, without obstructing vision of the driver.

Figure 4:
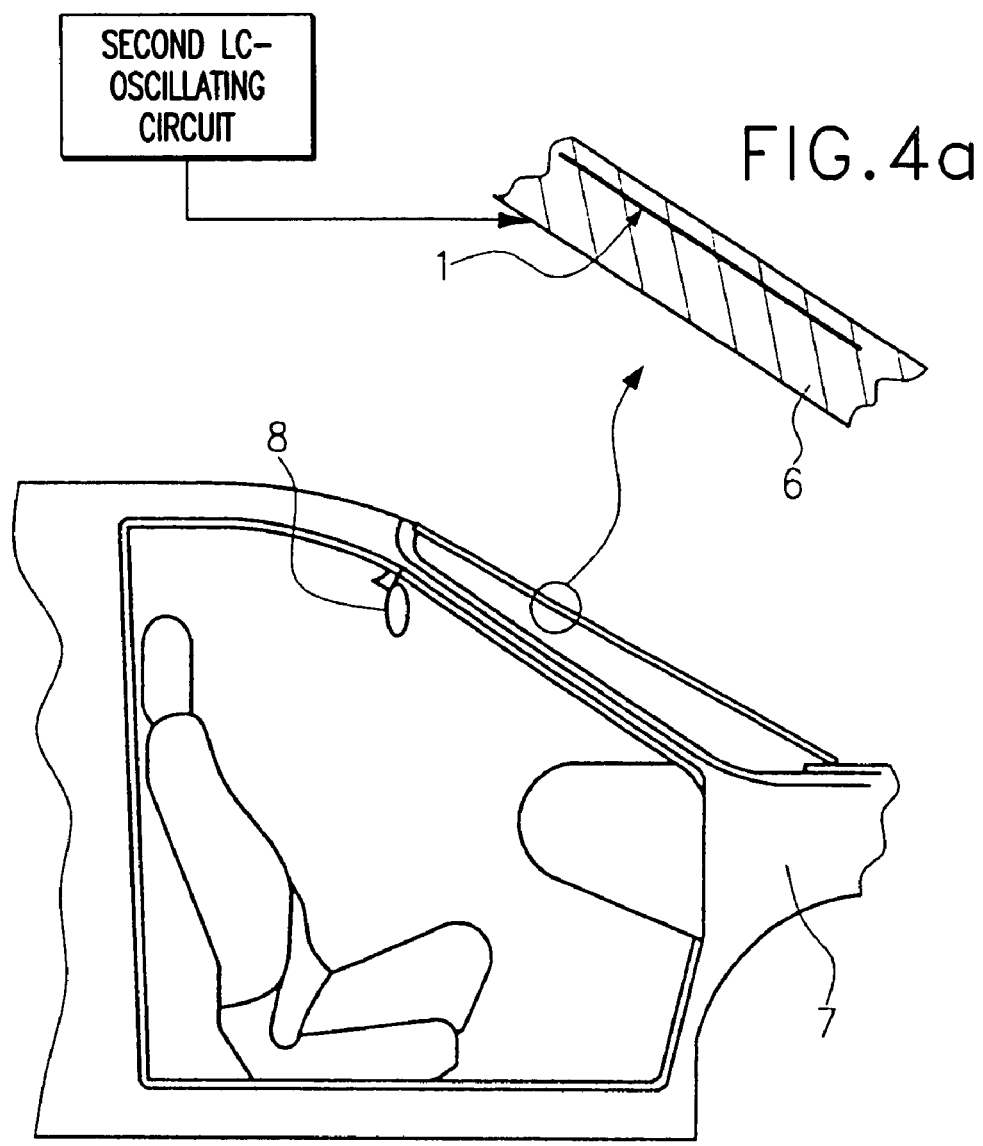
FIG. 4 is a cutaway schematic view of an arrangement of individual parts of an embodiment of a device for determining moisture of this invention in a motor vehicle.

In particular embodiments of devices of this invention for determining moisture, the transducer is integrated into a support. FIGS. 4 and 4a show this where a transducer 1 of only a single conductive lead is integrated into a front pane 6 of a motor vehicle 7. When the pane 6 is seen in cross section, the transducer 1 is arranged closer to an outwardly facing surface of the pane 6 than to a motor-vehicle interior facing other surface of the pane 6. The integration of the transducer 1 should, in this regard, in a beneficial manner, be as close to the moisture as possible. The smaller the spacing from the pane surface, the greater the change in the resonance frequency $f_0$ of the LC-oscillating circuit 1 with the degree of moisture.

In the embodiment of FIG. 4 of the device for determining moisture of this invention, the oscillator 2 with the tuning device 3 are integrated into an interior rearview mirror 8 of the motor vehicle.

Thus, this is an embodiment of the device for measuring moisture of this invention, in which the transducer 1 and the oscillator 2 have a contact-less, or contact-free, energy coupling. As can be easily seen, this provides a great deal of configuration freedom when the electrical components of this device are mounted. Thus, in further embodiments of such devices for determining moisture of this invention, the oscillator 2 can also be integrated into a roof 7 of the motor vehicle.

In many embodiments of the device for determining moisture of this invention, the spacing between the oscillator 2 and the transducer 1 is in a range from 1 cm to 1 m.

Further, in other embodiments of the device for measuring moisture of this invention at least one further LC-oscillating circuit 1 is provided as an additional transducer. Often, such an additional transducer, or one of additional transducers, provides a reference measurement. To produce a statement about an amount of rain, for example, upon use of one embodiment of the device for determining moisture of this invention, a frequency warping, or shifting, relative to normal air should be measured. The frequency difference between sensor and reference transducers provides then again the amount of rain to be determined. In various embodiments structured in this manner of devices for determining moisture of this invention, the individual oscillating circuits are arranged such that their natural frequencies do not cross in a range of from 0% to 100%.

Among the immediately-above-described embodiments having at least one additional LC-oscillating circuit as a further transducer, there are various embodiments of devices for determining moisture of this invention in which the first transducer 1 is mounted on one side of a support, for example on the windshield 6 of a motor vehicle, while the further transducer is mounted on a side of the support facing away from the first transducer 1. Similarly, upon integrating the transducers into the support, the first transducer 1 can then be arranged nearer to a front surface of the support while the additional transducer is integrated into the support nearer to a side facing away from the first-named front surface of the support.

In addition to the above-detailed uses of the embodiments of the devices for determining moisture of this invention as a rain sensor on motor vehicles, other embodiments of devices for determining moisture of this invention are particularly suitable for determining moisture in ovens.

I claim:

1. A device for determining moisture, said device including an LC-oscillating circuit as a first transducer and a second LC-oscillating circuit as a second transducer;
   an oscillator for exciting the first and second LC-oscillating circuits;
   a tuning circuit for sweep-wise tuning the frequency of the oscillator; and
   a measuring and evaluation circuit for recording a dampening or attenuation condition of the first LC-oscillator and for providing a signal that is dependent on an amount of moisture at or surrounding the first transducer;
   wherein the first and second transducers are coupled to the oscillator by a contact-free energy coupling.

2. A device for determining moisture, said device including: an LC-oscillating circuit as a first transducer and a second LC-oscillating circuit as a second transducer;
   an oscillator for exciting the first and second LC-oscillating circuits;
   a tuning device for sweep-wise tuning the frequency of the oscillator; and
   a measuring and evaluation circuit for detecting a dampening or attenuation condition of the first LC-oscillator and for providing a signal that is dependent on an amount of moisture at or surrounding the first transducer; wherein the first and second transducers are formed of a single conductive lead, respectively.

3. The device of claim 1, wherein the transducer is formed of a single conductive lead.

4. The device of claim 2, wherein the single conductive lead is arranged in one of a planar and coiled manner.

5. The device of claim 1, wherein the transducer is integrated into a support.

6. The device of claim 5, wherein the transducer is arranged closer to a front surface of the support than to an opposite surface of the support.

7. The device of claim 1, wherein the transducer is mounted on an outer surface of a support.

8. The device of claim 5, wherein the support is a window pane.

9. The device of claim 8, wherein the window pane is a pane of a motor vehicle.

10. The device of claim 1, wherein the second LC-oscillating circuit is used for taking a reference measurement.

11. The device of claim 1, wherein the oscillating circuits are so arranged that their natural frequencies do not cross in a range of from 0% to 100% moisture.

12. The device of claim 6, wherein the second LC-oscillating circuit is mounted on the opposite surface of the support.

13. The device of claim 9, wherein the oscillator is integrated into one of a mirror and a roof of the motor vehicle.

14. The device of claim 1, wherein a spacing between the oscillator and the transducer is in a range of from 1 cm to 1 m.

15. The device of claim 3, wherein the single conductive lead is arranged in one of a planar and coiled manner.

16. A device for generating and using a moisture signal as a rain sensor, comprising:
   an LC-oscillating circuit as a first transducer and a second LC-oscillating circuit as a second transducer;
   an oscillator for exciting the first and second LC-oscillating circuits;
   a tuning circuit for sweep-wise tuning the frequency of the oscillator; and
   a measuring and evaluation circuit for detecting a dampening or attenuation condition of the first transducer and for providing a signal that is dependent on an amount of moisture at or surrounding the first transducer the moisture being due to rain;
   wherein the first and second transducers are coupled to the oscillator by a contact-free energy coupling, and
   further comprising one or more devices to be controlled by the signal.

17. A device for generating and using a moisture signal as a rain sensor, comprising:
   an LC-oscillating circuit as a first transducer and a second LC-oscillating circuit as a second transducer;
   an oscillator for exciting the first and second LC-oscillating circuits;
   a tuning device for sweep-wise tuning the frequency of the oscillator; and
   a measuring and evaluation circuit for detecting a dampening or attenuation condition of the first transducer and for providing a signal that is dependent on an amount of moisture at or surrounding the first transducer, the moisture being due to rain; wherein the first and second transducers are formed of a single conductive lead, respectively; and
   further comprising one or more devices to be controlled by the signal.

18. The device of claim 17, wherein the one or more devices to be controlled comprise one or more windshield wipers, pumps, ventilators and/or indicators.

19. The device of claim 16, wherein the one or more devices to be controlled comprise one or more windshield wipers, pumps, ventilators and/or indicators.

* * * * *